(12) United States Patent
Mitchell

(10) Patent No.: US 7,115,423 B1  
(45) Date of Patent: Oct. 3, 2006

(54) FLUIDIC STRUCTURES WITHIN AN ARRAY PACKAGE

(75) Inventor: J. Robert Mitchell, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/426,111

(22) Filed: Oct. 22, 1999

(51) Int. Cl.  
*G01N 1/10* (2006.01)

(52) U.S. Cl. ............... 436/180; 436/174; 436/177; 422/58; 422/61; 422/68.1; 422/102; 422/103; 422/104

(58) Field of Classification Search .......... 422/58, 422/61, 68.1, 81, 82.05, 102–104, 131; 435/287.1–287.3, 435/288.3–288.5; 436/164–165, 177, 180; 347/61, 62, 65, 92  
See application file for complete search history.

(56) References Cited

U.S. PATENT DOCUMENTS

| | | | |
|---|---|---|---|
| 4,795,562 A | 1/1989 | Walsh | 210/232 |
| 4,871,463 A | 10/1989 | Taylor et al. | 210/161 |
| 5,122,142 A | 6/1992 | Pascaloff | 606/82 |
| 5,273,905 A | 12/1993 | Muller et al. | 435/301 |
| 5,384,261 A * | 1/1995 | Winkler et al. | 436/518 |
| 5,427,663 A * | 6/1995 | Austin et al. | 204/549 |
| 5,624,815 A | 4/1997 | Grant et al. | 435/30 |
| 5,699,462 A | 12/1997 | Fouquet et al. | 385/18 |
| 5,849,486 A | 12/1998 | Heller et al. | 435/6 |
| 5,856,174 A | 1/1999 | Lipshutz et al. | 435/286.5 |
| 5,882,595 A | 3/1999 | La Motte | 422/65 |
| 5,922,591 A | 7/1999 | Anderson et al. | 435/287.2 |
| 5,972,721 A * | 10/1999 | Bruno et al. | 436/526 |
| 6,062,681 A * | 5/2000 | Field et al. | 347/65 |
| 6,184,030 B1 * | 2/2001 | Katoot et al. | 435/287.2 |
| 6,225,109 B1 * | 5/2001 | Juncosa et al. | 435/288.5 |
| 6,287,850 B1 * | 9/2001 | Besemer et al. | 435/287.2 |
| 6,299,673 B1 | 10/2001 | Field et al. | |
| 6,307,042 B1 * | 10/2001 | Goldberg et al. | 536/25.3 |
| 6,360,775 B1 | 3/2002 | Barth et al. | |
| 6,398,850 B1 | 6/2002 | Field et al. | |

FOREIGN PATENT DOCUMENTS

WO WO-9630124 A1 * 10/1996

OTHER PUBLICATIONS

Jun, Thomas K. Valveless pumping using traversing vapor bubbles in microchannels, Jun. 1998, Journal of Applied Physics, vol. 83, No. 11, pp 5658–5663.*

* cited by examiner

*Primary Examiner*—Jill Warden  
*Assistant Examiner*—Dwayne K Handy

(57) ABSTRACT

A package for an addressable array of multiple features carried on a first side of a substrate, and a method of using such package. The package includes a housing which receives the substrate such that the housing and received substrate define a chamber into which the multiple features face, and which chamber is accessible through a first port. The housing includes a first set of multiple fluid distribution channels each disposed between the first port and the multiple features of the received substrate so as to direct fluid flow between multiple different regions across the first side of the received substrate to or from the first port. The fluid distribution channels may be valved such as by being capillary sized or by being provided with a bubble formation device (such as a nucleating resistor). The channels can provide for an even flow of wash fluid across the array while confining sample to the region of the array.

19 Claims, 2 Drawing Sheets

FLUIDIC STRUCTURES WITHIN AN ARRAY PACKAGE

FIELD OF THE INVENTION

This invention relates to arrays, particularly biopolymer arrays such as DNA arrays, which are useful in diagnostic, screening, gene expression analysis, and other applications.

BACKGROUND OF THE INVENTION

Polynucleotide arrays (such as DNA or RNA arrays), are known and are used, for example, as diagnostic or screening tools. Such arrays include features (sometimes referenced as spots or regions) of usually different sequence polynucleotides arranged in a predetermined configuration on a substrate. The arrays, when exposed to a sample, will exhibit a binding pattern. The array can be interrogated by observing this binding pattern by, for example, labeling all polynucleotide targets (for example, DNA) in the sample with a suitable label (such as a fluorescent compound), and accurately observing the fluorescent signal on the array. Assuming that the different sequence polynucleotides were correctly deposited in accordance with the predetermined configuration, then the observed binding pattern will be indicative of the presence and/or concentration of one or more polynucleotide components of the sample. Peptide arrays can be used in a similar manner.

Biopolymer arrays can be fabricated using either in situ synthesis methods or deposition of the previously obtained biopolymers. The in situ synthesis methods include those described in U.S. Pat. No. 5,449,754 for synthesizing peptide arrays, as well as WO 98/41531 and the references cited therein for synthesizing polynucleotides (specifically, DNA). The deposition methods basically involve depositing biopolymers at predetermined locations on a substrate which are suitably activated such that the biopolymers can link thereto. Biopolymers of different sequence may be deposited at different feature locations on the substrate to yield the completed array. Washing or other additional steps may also be used. Procedures known in the art for deposition of polynucleotides, particularly DNA such as whole oligomers or cDNA, are described, for example, in U.S. Pat. No. 5,807,522 (touching drop dispensers to a substrate), and in PCT publications WO 95/25116 and WO 98/41531, and elsewhere (use of an ink jet type head to fire drops onto the substrate).

In array fabrication, the quantities of DNA available for the array are usually very small and expensive. Sample quantities available for testing are usually also very small and it is therefore desirable to simultaneously test the same sample against a large number of different probes on an array. These conditions require use of arrays with large numbers of very small, closely spaced features. However, a housing may be provided to contain the array in a chamber which will be loaded with the sample to be tested, and which can be readily flushed to wash the array, as required. This requires fluid entrance and exit structures for wash fluids and the sample. A conventional entrance and exit port will generally not provide for uniform exposure of the array to the fluid being loaded into the chamber. Furthermore, such conventional structures will remain full of sample which is not exposed to the array and is essentially wasted.

The present invention realizes that it would be desirable then, to provide an array package with a chamber, into which a sample can be provided with little sample wastage in inlet or outlet structures. The present invention further realizes that it would also be desirable to provide such a package into which fluids, such as wash fluids, can be introduced relatively rapidly and in a manner which will more evenly move across the array.

SUMMARY OF THE INVENTION

The present invention realizes that by providing appropriately configured fluid channels between a port of an array package and the array in the chamber, sample fluid can be retained for contact with the array without portions being wasted in inlet or outlet structures. Furthermore, such channels can aid in liquid distribution over the array.

The present invention then, provides a package for an addressable array of multiple features carried on a first side of a substrate. The package includes a housing which receives the substrate such that the housing and received substrate define a chamber into which the multiple features face, and which chamber is accessible through a first port. The housing includes a first set of multiple fluid distribution channels each disposed between the first port and the multiple features of the received substrate so as to direct fluid flow between multiple different regions across the first side of the received substrate to or from the first port. Note that optionally, the package may include the received substrate. In such case, the received substrate carrying the multiple features, may be distinguishable from the remainder of the housing (as having been removably or fixedly mounted thereon, for example by means of adhesive, or of different material therefrom), or indistinguishable from the housing (as by being formed integrally with, and of the same material as, a part or all of the housing).

The housing may optionally further include a second port on a side of the multiple fluid distribution channels opposite that of the first port, as well as a second set of multiple fluid distribution channels each disposed between the second port and the multiple features of the received substrate so as to direct fluid flow between multiple different regions across the first side of the received substrate to or from the second port. A third port may also be provided, which accesses the chamber at a position between the first and second sets of fluid distribution channels.

While the features of the array may include any moieties desired they may, for example, include different biopolymer sequences (for example, polynucleotides such as DNA or RNA, or peptides) at different features (although some or all of the features could have the same sequences, as desired).

In one aspect, at least some (including all) of the fluid distribution channels of at least one (including both) sets, are provided with a valve by being capillary sized so that capillary action therein will retain fluid in the chamber in the absence of a minimal pressure differential applied across those fluid distribution channels. This minimal pressure differential is that required to overcome capillary action in the channels to push fluid therethrough. Thus, such valves are closed by providing a pressure differential below the minimal value, and opened by providing a pressure differential of at least the minimal value.

In another aspect, the package can additionally include a valve in the form of a bubble formation device (such as a nucleating resistor, which by definition is electrically operated) in at least some (including all) of the fluid distribution channels of at least one (including both) of the first and second sets, so that when activated a bubble is formed in the corresponding channel to retain fluid in the chamber.

Various configurations of the fluid channels are possible, For example, the multiple fluid distribution channels may be disposed between a port and the chamber such that fluid flow width increases between the first port to the first set of fluid distribution channels. For example, where the port is essentially one point or circle of a given diameter, the line may be longer than the diameter. Any (including all) of the ports may have a closure member normally closing the corresponding port. Such a closure member may be in the form of a resilient self-sealing member, for example a rubber septum.

The present invention further provides a method of exposing an addressable array of the above described type to a fluid. The method includes either adding or removing the fluid through the first port such that fluid flow is directed by the multiple fluid distribution channels between multiple different regions across the first side of the received substrate to or from the first port. The method may also include closing the valves in the channels so that fluid (for example, a sample fluid) will be retained in the chamber (that is, without passing out through the channels). In the case where the valves are the capillary sized distribution channels, the method may particularly then include providing less than the minimal pressure differential across those fluid distribution channels. In the case where the valves are the bubble formation devices, the method may particularly then include activating the bubble formation devices.

A sample to which the array is exposed in the present methods, may have been obtained from a location remote from a first location at which the array is exposed to the sample. Further, whether the array was obtained from the first or remote location, the array may be interrogated following exposure to the sample to obtain a result of the exposure (for example, the binding pattern), and this result or a conclusion based on the result communicated to a location remote from the first location (which may be the same or different from the remote location from which the sample was obtained).

In a particular application of the method, a first fluid to be tested by the array is added to the chamber through the third port. The valves in the channels can then be closed so as to retain the fluid in the chamber. A wash fluid is added through the first port such that the wash fluid is directed by the first set of fluid distribution channels from the first port toward multiple different regions across the first side of the substrate, and fluid exhausted through the second port. During the washing and exhaust steps the valves in the channels may be opened as described above.

In one aspect of the method, where channels are valved, they can be selectively activated (that is opened and closed) either continuously and/or in some sequence to control flow of fluid through them in a desired pattern (for example, to aid in washing of the array).

The method and apparatus of the present invention can provide any one or more of a number of useful benefits, such as the following benefits. For example, the use of the capillary sized channels, the channels with bubble formation devices, or channels with other valves in them, or any combination of these, fluid (particularly sample fluid which may have been added through the third port) can be confined to the chamber where the array is located. This can reduce the amount of sample fluid out of contact with the array by occupying fluid inlet or outlet structures. The channels can also serve to guide fluid (such as wash fluid) into or out of the array containing chamber.

BRIEF DESCRIPTION OF THE DRAWINGS

Embodiments of the invention will now be described with reference to the drawings, in which.

To facilitate understanding, the same reference numerals have been used, where practical, to designate similar elements that are common to the FIGS.

DETAILED DESCRIPTION OF THE INVENTION

Figure 1:
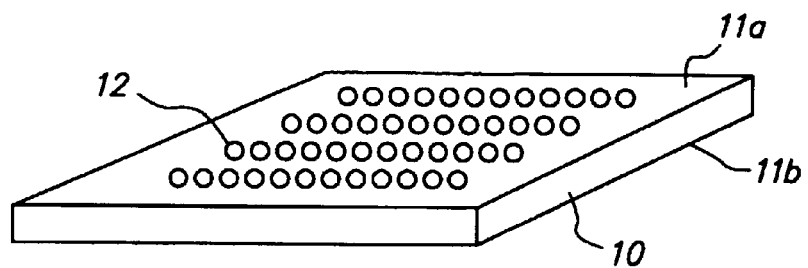
FIG. 1 is a perspective view of a substrate carrying a typical array, as may be used with, or part of, a package of the present invention.

Throughout the present application, unless a contrary intention appears, the terms following terms refer to the indicated characteristics. A "biopolymer" is a polymer of one or more types of repeating units. Biopolymers are typically found in biological systems and particularly include peptides or polynucleotides, as well as such compounds composed of or containing amino acid or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as analogs (whether synthetic or naturally occurring) of such sub-units. For example, a "biopolymer" includes DNA (including cDNA), RNA, oligonucleotides, and PNA and other oligonucleotides as described in U.S. Pat. No. 5,948,902 and references cited therein (all of which are incorporated herein by reference), regardless of the source. An "oligonucleotide" generally refers to a polynucleotide of about 10 to 100 nucleotides (or other units) in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution). An "addressable array" includes any one or two dimensional arrangement of discrete regions (or "features") bearing particular moieties (for example, different polynucleotide sequences) associated with that region and positioned at particular predetermined locations on the substrate (each such location being an "address"). These regions may or may not be separated by intervening spaces. A "chamber" references an enclosed volume (although a chamber may be accessible through one or more ports). By one thing being "remote" from another, is referenced that they the two items are at least in different buildings, and more typically are separated by at least one mile, at least ten miles, or at least one hundred miles. It will also be appreciated that throughout the present application, that words such as "top", "upper", and "lower" are used in a relative sense only. "Fluid" is used herein to reference a liquid. "Venting" or "vent" includes the outward flow of a gas or liquid. Reference to a singular item, includes the possibility that there are plural of the same items present. All patents and other cited references are incorporated into this application by reference.

Figure 2:
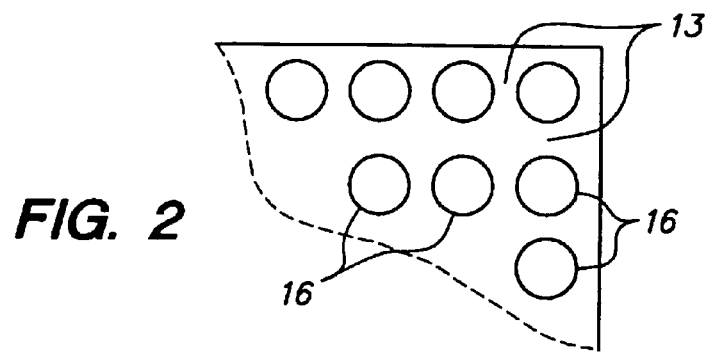
FIG. 2 is an enlarged view of a portion of FIG. 1 showing some of the identifiable individual regions of a single array of FIG. 1.
Figure 3:
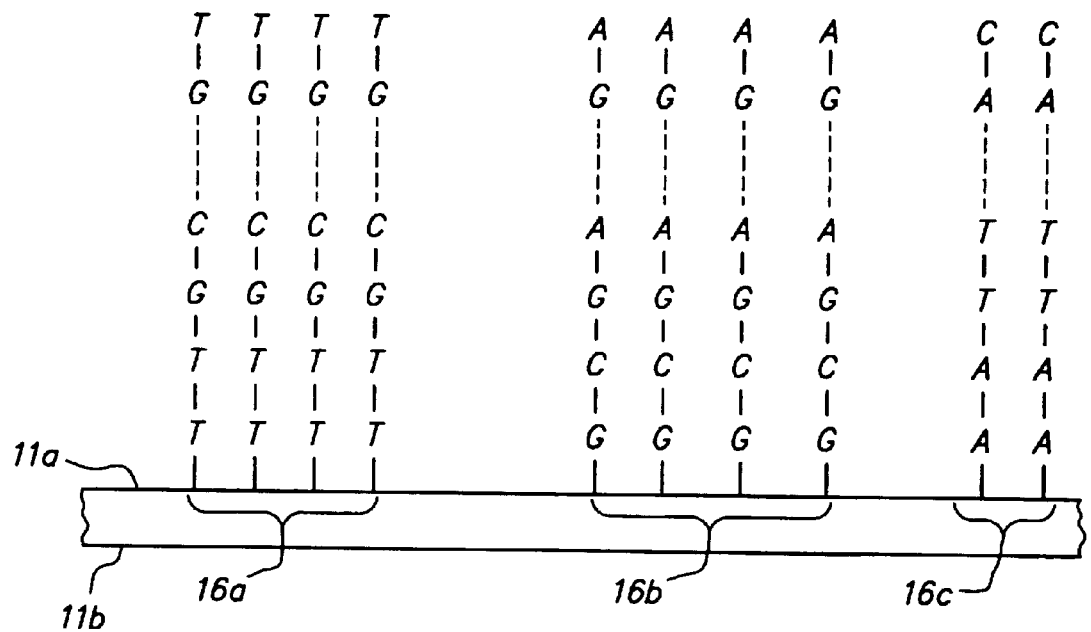
FIG. 3 is an enlarged cross-section of a portion of FIG. 2.

Referring first to FIGS. 1–3, a contiguous planar transparent substrate 10 carries multiple features 16a, 16b, 16c (collectively referenced as features 16) disposed across a first surface 11a of substrate 10 and separated by areas 13. A second surface 11b of substrate 10 does not carry any features. Substrate 10 may he of any shape although the remainder of the package of the present invention may need to be adapted accordingly. A typical array may contain at least ten features 16, or at least 100 features, at least 10,000 features, or more. All of the features 16 may be different, or some or all could be the same. Each feature carries a predetermined moiety or mixture of moieties which in the case of FIGS. 1–3 is a polynucleotide having a particular sequence. This is illustrated schematically in FIG. 3 where regions 16 are shown as carrying different polynucleotide sequences. Arrays of FIGS. 1–3 can be manufactured by in situ or deposition methods as discussed above.

Figure 4:
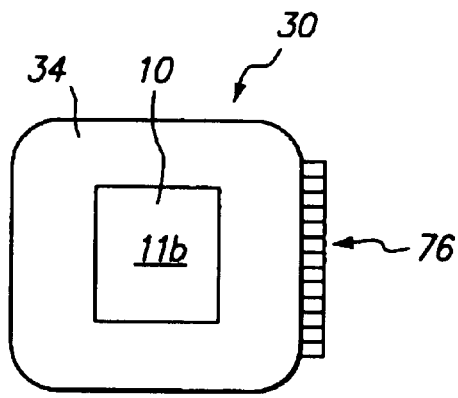
FIG. 4 is a top view of an array package of the present invention (including the substrate carrying the array)
Figure 5:
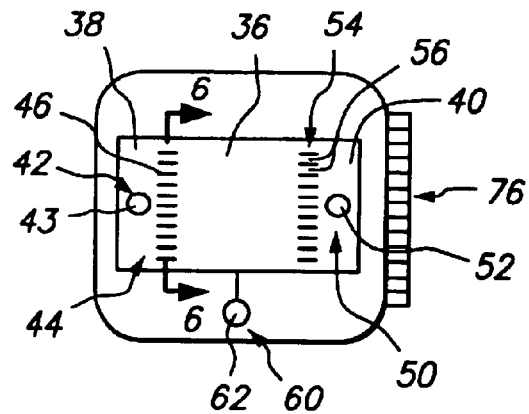
FIG. 5 is a partially cut away top view of the package of FIG. 4.
Figure 6:
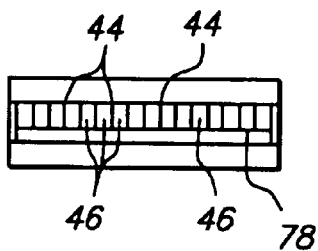
FIG. 6 is a cross-section along the line 6—6 of FIG. 4.

Referring now to FIGS. 4–6, an array package 30 includes a housing 34 which has received substrate 10 adjacent an opening. Substrate 10 is sealed (such as by the use of a suitable adhesive) to housing 34 with the second surface 11b facing outward. Housing 34 is configured such that housing 34 and substrate 10, define a chamber 36 into which features 16 of array 12 face. Housing 34 also includes at one end, a first port communicating with a cavity 38 and a first set of fluid distribution channels 46 defined between a series of upright baffles 44. In a similar manner, a second port 50 communicates through a cavity 40 into a second set of fluid distribution channels 56 defined between a series of upright baffles 54. First and second ports 42, 50 include respective closure members in the form of resilient self-sealing rubber septa 43, 52 which normally close respective ports. In the foregoing manner, both first and second ports 42, 50 can access chamber 36 through respective cavities 38, 40 and first and second sets of distribution channels. Note that channels 46 are disposed such that fluid flow width increases between the first set 46 and first port 42. Similarly fluid flow width also increases between the second set 56 and the second port 50. That is, in the specific arrangement shown, the line along which all of channels 46 or 56 lie is longer than the diameter of the corresponding port. A third port 60 also accesses chamber 36 at a position mid-way between the first and second sets of fluid distribution channels 46, 56. Third port 60 also includes a closure members in the form of a resilient self-sealing rubber septa 62 which normally closes third port 60.

Figure 7:
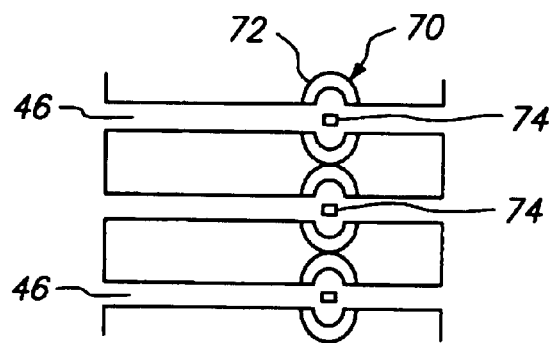
FIG. 7 is an enlarged view of fluid distribution channels of an array package of the present invention, incorporating bubble nucleating resistors.

As can be seen particularly from FIG. 5, first and second sets of channels 46, 56 are positioned in opposed relationship across chamber 36 and just outside the area covered by array 12. In this manner channels 46 and 56 can direct fluid flow between multiple different regions of chamber 36 across the first side 11a of substrate 10, to or from their first and second ports 42, 50, respectively. Furthermore, channels 46, 54 are valved such that they can prevent or permit fluid flow out of the chamber to the first or second port. This can be accomplished in a number of alternative constructions. In one construction, channels 46, 54 are capillary sized so that capillary action of fluid in them will retain fluid in chamber 36 in the absence of a minimal pressure applied across (that is, from one opening of the channels to the other) those channels. Application of at least the minimal pressure causes fluid to be pushed through those channels. In another construction illustrated in detail in FIG. 7, channels 46, 54 are additionally or alternatively provided with a bubble formation valve which includes a bubble formation device in the form of electrically operated bubble nucleating resistors 74 and associated enlarged regions 72 of channels 46. Note that when active valves such as the bubble formation valves are provided (versus relying on capillary dimension of channels 46 or 56) channels 46 or 56 may be larger than capillary sized. While FIG. 7 is referenced as showing channels 46, the same construction can be used in channels 54 also. Activation of resistors 74 causes a bubble to form and be trapped in regions 72, thereby closing the channels and retaining fluid in chamber 36. The channels can be re-opened by applying sufficient pressure across them to break the bubble seal or by using other means to collapse the bubble.

In a typical method of exposing the addressable array 12 using the package 30, a first fluid to be tested by the array 12 (which may either be a reference or trial sample) may be added to (that is, loaded into) first chamber 36 through third port 60 by inserting a hypodermic needle (or other mechanism, such as a rigid pipette) in communication with a sample source, through septum 62. Note that the first fluid so loaded goes directly into chamber 36 to contact array 12. During this loading operation, hollow needles (or other equivalent venting devices) are inserted through septa 43, 52 of first and second ports 42, 50, respectively, such that chamber 36 may vent through channels 46, 56. In the case where channels 46, 56 are capillary, when the first fluid has filled chamber 36 and channels 46, 56, capillary action in those channels will retain the first fluid in chamber 36 provided the source of the first fluid does not provide a pressure across the channels which is greater than the minimal pressure necessary to overcome such capillary action. In the case where nucleating resistors 74 are used, these are activated by an external processor. The processor delivers the requisite electrical signals or pulses through electrical connector 76 and electronics support substrate 78, to form a bubble seal and close channels 46, 56 so as to retain fluid in chamber 36 provided the source of the first fluid does not provide a pressure across channels 46, 56 sufficient to overcome the bubble seal. The external processor may either be synchronized with the loading operation to activate resistors 74 at the correct time, or resistors 74 may simply be activated continuously during the loading operation (since a bubble will not be formed until fluid flows down the channels). Note that energy transferred to the resistors will typically be insignificant relative to the thermal mass of the loaded fluid, and should not significantly effect the temperature of it.

When loading is completed, the needles optionally may be removed from their respective septa 43, 52, 62 and the package exposed to whatever conditions are required to complete any reaction between the first fluid and array 12. For example, during polynucleotide hybridization in the case of a polynucleotide array, the temperature will typically be maintained at an elevated temperature for multiple hours, for example between about 35 to 95° C. (more preferably between 40 to 95° C., and most preferably between 45 to 65° C.) for 0.5 to 48 hours (more preferably between 2 to 40 hours; and most preferably between 5 to 16 hours).

However, it will be appreciated that such conditions should preferably not induce a pressure differential across channels 46, 56 which would be sufficient to cause the seal in those channels to be broken and first fluid drained from chamber 36 (that is, less than the minimal pressure is provided following loading).

After the reaction with array 12 is deemed to be sufficiently complete, a hollow needle in communication with a source of suitable wash fluid (such as an aqueous buffer solution) can be inserted through septa 43 of first port 42, while another hollow needle is inserted through septa 52 of second port 50 to allow for venting. The wash fluid is then forced from first port 42 through cavity 38 under sufficient pressure that the previously established seals in channels 46 and 56 are broken (that is, the pressure is greater than the minimal pressure for all the channels). Thus, the wash fluid so added through first port 42 will be directed by the first set of channels 46 from first port 42 toward multiple different regions across first side 11a of substrate 10. Note that if positive valves such as provided by nucleating resistors 74 are present in first set of channels 46, they can be selectively activated (that is opened and closed) either continuously and/or in some sequence, to control the flow of wash fluid to different areas of array 12, so as to enhance coverage of the wash process. The first fluid (and, depending on how long it is desired to continue the operation, wash fluid also) will be vented from chamber 36 through the second set of channels 56 and out second port 50 (and the hollow needle inserted through septum 52). Optionally, septa 43, 52 can be removed at this point, to increase fluid flow.

Following the above and prior to interrogating array 12, all fluid can be vented from chamber 36 to dry array 12, such as by spinning package 30 to empty the chamber by centrifugal force (in which case needles or pipette tips can remain through septa 43, 52 with a slight negative pressure applied through them, or the septa could be removed). Alternatively, air or other gas could be blown through first port 42 and out second port 50. The dried array 12 can then be interrogated by directing a light beam toward second side 11b of array 12. Interrogation of dried arrays is described in U.S. Pat. No. 5,922,534. Provided substrate 10 is sufficiently transparent to both the wavelength of the irradiating light and the wavelength of light emitted back from array 12 on first side 11a, the interrogation can be performed with substrate 10 remaining in housing 34. If substrate 10 is not so transparent, and there is no other way of conveniently interrogating array 12, substrate 10 can be removed from housing 34.

In order to obtain the above mentioned capillary action, the size of channels 46 or 56 will be suitably small depending on some extent on the characteristics of the first fluid (such as surface tension), although in a typical case the first fluid will be an aqueous solution. Further, in general (whether capillary action is relied upon or not) channels 46, 56 will have a length and width which can vary depending on a wide range of factors, including hybridization temperatures, insertion pressures and fluid viscosity (to some degree). Typically channels 46 or 56, to exhibit the capillary action while still allowing liquid to flow through them at a sufficient rate, will have a cross-sectional area of between 10 sq µm to 4 sq mm, preferably between 100 sq µm and 1 sq mm. While channels 46, 56 in the embodiment of FIGS. 5–7 have a square cross-section, they could have a cross-section of any other suitable shape (for example, rectangular, circular or elliptical). As to the length of channels 46, 56, each will typically be between 1 mm to 20 mm, preferably between 5 mm to 10 mm. In the case where enlarged regions 72 are present, each may define a volume of between 0.1 µl to 100 µl, preferably between 1 µl to 10 µl. Chamber 36, is substantially equal in length and width to the length and width of substrate 10. As to the thickness of chamber 36 (defined by the maximum distance between first surface 11a of substrate 10 and a back surface of chamber 36 defined by housing 34), this may for example be no greater than 5 mm (or no greater than 2 mm or 1 mm), and no less than 0.2 or 0.5 mm or even 0.75 mm. Nucleating resistors 74 may each be of a size and type typically found in an inkjet head. Activation of nucleating resistors 74 results in raising the temperature of them sufficiently to vaporize a portion of the fluid immediately adjacent the heater and produce the bubble. The temperature of the resistors 74 is raised to a temperature at least about 100° C., usually at least about 400° C. and more usually at least about 700° C., and the temperature may be raised as high as 1000° C. or higher, but is usually raised to a temperature that does not exceed about 2000° C. and more usually does not exceed about 1500° C. Accordingly, a sufficient amount of energy will be delivered to the nucleating resistors 74 to produce the requisite temperature rise, where the amount of energy is generally in the range about 1.0 to 100 µJ, usually about 1.5 to 15 µJ.

The components of the embodiments of the package 30 described above, may be made of any suitable material. For example, housing 34 can be made of metal or plastic such as polypropylene, polyethylene or acrylonitrile-butadiene-styrene ("ABS"). Substrate 10 may be of any suitable material, and is preferably sufficiently transparent to the wavelength of an interrogating and array emitted light, as to allow interrogation without removal from housing 34. Such transparent and non-transparent materials include, for flexible substrates: nylon, both modified and unmodified, nitrocellulose, polypropylene, and the like. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like). The materials from which substrate 10 and housing 34 (at least the portion facing toward the inside of chamber 36) may be fabricated should ideally themselves exhibit a low level of binding during hybridization or other events.

Modifications in the particular embodiments described above are, of course, possible. For example, any of a variety of geometries of the features 16 may be constructed other than the organized rows and columns of array 12 of FIGS. 1–3. For example, features 16 can be arranged in a series of curvilinear rows across the substrate surface (for example, a series of concentric circles or semi-circles of spots), and the like. Even irregular arrangements of features 16 can be used, at least when some means is provided such that during their use the locations of regions of particular characteristics can be determined (for example, a map of the regions is provided to the end user with the array). Furthermore, substrate 10 could carry more than one array 12, arranged in any desired configuration on substrate 10. While substrate 10 is planar and rectangular in form, other shapes could be used with housing 34 being adjusted accordingly. In many embodiments, substrate 10 will be shaped generally as a planar, rectangular solid, having a length in the range about 4 mm to 200 mm, usually about 4 mm to 150 mm, more usually about 4 mm to 25 mm; a width in the range about 4 mm to 200 mm, usually about 4 mm to 120 mm and more usually about 4 mm to 25 mm; and a thickness in the range about 0.01 mm to 5.0 mm, usually from about 0.1 mm to 2 mm and more usually from about 0.9 to 1.1 mm. However, larger substrates can be used. Less preferably, substrate 10 could have three-dimensional shape with irregularities in first surface 11*a*. In any event, the dimensions of housing 34 may be adjusted accordingly.

Various modifications to the embodiments of the particular embodiments described above are, of course, possible. Accordingly, the present invention is not limited to the particular embodiments described in detail above.

What is claimed is:

1. A method of exposing an addressable array of multiple features carried on a first side of a substrate, to a fluid, using a housing and the substrate together so as to define a chamber into which the multiple features face, and which chamber is accessible through a first port, the housing including a first set of multiple fluid distribution channels each disposed between the first port and the chamber of the received substrate, the method comprising:

either adding or removing the fluid through the first port such that fluid flow is directed by the multiple fluid distribution channels between multiple different regions across the first side of the received substrate to or from the first port;

wherein the fluid distribution channels are capillary sized so that capillary action therein will retain fluid in the chamber in the absence of a minimal pressure differential applied across those fluid distribution channels.

2. A method according to claim 1 wherein the features comprise different biopolymer sequences.

3. A method according to claim 1 wherein the fluid is a sample to be tested by the array, the method additionally comprising interrogating the array following exposure.

4. A method according to claim 1 wherein the fluid is a sample to be tested by the array and the array is exposed to the sample at a first location, the method additionally comprising interrogating the array following exposure to obtain a result of the exposure, and communicating the result or a conclusion based on the result to a location remote from the first location.

5. A method according to claim 4 wherein the sample was obtained from a location remote from the first location.

6. A method of exposing an addressable array of multiple features carried on a first side of a substrate, to a fluid, using a housing and the substrate together so as to define a chamber into which the multiple features face, and which chamber is accessible through a first port, the housing including a first set of multiple fluid distribution channels each disposed between the first port and the chamber of the received substrate, the method comprising:

either adding or removing the fluid through the first port such that fluid flow is directed by the multiple fluid distribution channels between multiple different regions across the first side of the received substrate to or from the first port;

wherein the package additionally has a bubble formation device in at least some of the fluid distribution channels of the first set, the method additionally comprising activating the bubble formation device in at least one of the fluid distribution channels so as to form a bubble is formed in the corresponding channel to retain fluid in the chamber.

7. A method according to claim 6 wherein the fluid is a sample to be tested by the array, the method additionally comprising interrogating the array following exposure.

8. A method according to claim 6 wherein the fluid is a sample to be tested by the array and the array is exposed to the sample at a first location, the method additionally comprising interrogating the array following exposure to obtain a result of the exposure, and communicating the result or a conclusion based on the result to a location remote from the first location.

9. A method according to claim 8 wherein the sample was obtained from a location remote from the first location.

10. A package for an addressable array of multiple features carried on a first side of a substrate, comprising a housing which receives the substrate such that the housing and received substrate define a chamber into which the multiple features face, and which chamber is accessible through a first port, the housing including a first set of multiple fluid distribution channels each disposed between the first part and the chamber so as to direct fluid flow between multiple different regions across the first side of the received substrate to or from the first port;

wherein at least some of the fluid distribution channels are valved so as to be selectively closable or openable to prevent or permit fluid flow out of the chamber to the first port.

11. A package according to claim 10, additionally comprising a bubble formation device in at least some of the fluid distribution channels of the first set, so that when activated a bubble is formed in the corresponding channel to retain fluid in the chamber.

12. A package according to claim 11, wherein the bubble formation device comprises a bubble nucleating resistor.

13. A package according to claim 10 wherein the first port includes a closure member normally closing the first port.

14. A package according to claim 13 wherein the closure member comprises a resilient self-sealing member.

15. A package for an addressable array of multiple features carried on a first side of a substrate, comprising a housing which receives the substrate such that the housing and received substrate define a chamber into which the multiple features face, and which chamber is accessible through a first port, the housing including a first set of multiple fluid distribution channels each disposed between the first port and the chamber so as to direct fluid flow between multiple different regions across the first side of the received substrate to or from the first port;

wherein at least some of the fluid distribution channels are capillary sized so that capillary action therein will retain fluid in the chamber in the absence of a minimal pressure differential applied across those fluid distribution channels.

16. A package according to claim 15, additionally comprising the received substrate.

17. A package according to claim 16 wherein the features comprise different biopolymer sequences.

18. A package according to claim 17 wherein the features comprise different DNA sequences.

19. A package according to claim 15 wherein fluid flow width increases between the first port to the first set of fluid distribution channels.

* * * * *